US012767941B2

(12) United States Patent
Jiang et al.

(10) Patent No.: US 12,767,941 B2
(45) Date of Patent: Oct. 20, 2026

(54) METHOD FOR THE EFFICIENT EXPRESSION AND PURIFICATION AND APPLICATION OF A RECOMBINANT FUSION PROTEIN OF MANNase AND HOMOLOGUES THEREOF AND GLP-1

(71) Applicant: ANHUI NEW SIMON BIOTECH CO., LTD., Anhui (CN)

(72) Inventors: Wei Jiang, Anhui (CN); Huiqiang Lou, Anhui (CN); Yan Wang, Anhui (CN); Weixiong Yu, Anhui (CN); Chong Xu, Anhui (CN)

(73) Assignee: ANHUI NEW SIMON BIOTECH CO., LTD., Anhui (CN)

( * ) Notice: Subject to any disclaimer, the term of this patent is extended or adjusted under 35 U.S.C. 154(b) by 782 days.

(21) Appl. No.: 18/020,429

(22) PCT Filed: Jan. 26, 2021

(86) PCT No.: PCT/CN2021/073745

§ 371 (c)(1),
(2) Date: Feb. 9, 2023

(87) PCT Pub. No.: WO2022/032991

PCT Pub. Date: Feb. 17, 2022

(65) Prior Publication Data

US 2023/0295594 A1 Sep. 21, 2023

(30) Foreign Application Priority Data

Aug. 10, 2020 (CN) ......................... 202010795389.9

(51) Int. Cl.

| | |
|---|---|
| ***C12N 9/24*** | (2006.01) |
| ***C07K 14/605*** | (2006.01) |
| ***C12N 1/165*** | (2026.01) |
| ***C12N 15/81*** | (2006.01) |

(52) U.S. Cl.

CPC .......... *C12N 9/2488* (2013.01); *C07K 14/605* (2013.01); *C12N 1/165* (2021.05); *C12N 15/815* (2013.01); *C12Y 302/01025* (2013.01)

(58) Field of Classification Search

None

See application file for complete search history.

(56) References Cited

FOREIGN PATENT DOCUMENTS

| | | | |
|---|---|---|---|
| CN | 1927888 | 3/2007 | |
| CN | 105884901 | 8/2016 | |
| CN | 106008717 | 10/2016 | |
| CN | 109628479 | 4/2019 | |
| CN | 111909955 | 11/2020 | |
| EP | 1408050 B1 * | 9/2009 | .......... C07K 14/605 |
| EP | 2331072 | 6/2011 | |

OTHER PUBLICATIONS

CN 1927888 translation provided by Google Patents (20 pages). (Year: 2007).*

CN 1834237 translation provided by Google Patents (14 pages). (Year: 2006).*

Zhongkai Zhou; et al., "Regulation of hyperglycemia in diabetic mice by autolysates from B-mannanase-treated brewer's yeast," Journal of the Science of Food and Agriculture, vol. 99, Issue15, Dec. 2019, pp. 6981-6988.

Jie Zhang; et al., "Research progress of B-mannanase," Heilongjiang Medicine Journal, vol. 24, No. 2, Feb. 2011, pp. 248-250.

"International Search Report (Form PCT/ISA/210) of PCT/CN2021/073745," mailed on May 14, 2021, with English translation thereof, pp. 1-8.

"Written Opinion of the International Searching Authority (Form PCT/ISA/237) of PCT/CN2021/073745," mailed on May 14, 2021, pp. 1-5.

* cited by examiner

*Primary Examiner* — Marsha Tsay

(74) *Attorney, Agent, or Firm* — JCIPRNET

(57) ABSTRACT

The invention relates to method for the efficient expression and purification and application of a recombinant fusion protein of MANNase and homologues thereof and GLP-1. Through genetic recombination technology, soluble proteins are obtained by using high density fermentation of *Pichia pastoris* to induce secretory expression, followed by isolation and purification by filtration and concentration to obtain high yield of target proteins. The high fermentation expression and simple isolation steps solve the limitations of the current GLP-1 analogs such as low drug yield, high cost and the need for frequent injections. More importantly, the fusion protein has hypoglycemic effect not only by injection, but also by oral administration for hypoglycemia and weight reduction, which has good application value in obese and pre-diabetic patients. It also provides a basis for further research on the mechanism of hypoglycemia and weight loss of mannanase and homologues thereof with GLP-1 recombinant fusion protein.

9 Claims, 6 Drawing Sheets

Specification includes a Sequence Listing.

METHOD FOR THE EFFICIENT EXPRESSION AND PURIFICATION AND APPLICATION OF A RECOMBINANT FUSION PROTEIN OF MANNase AND HOMOLOGUES THEREOF AND GLP-1

CROSS-REFERENCE TO RELATED APPLICATION

This is a 371 application of the International PCT application serial no. PCT/CN2021/073745, filed on Jan. 26, 2021, which claims the priority benefits of China Application No. 202010795389.9, filed on Aug. 10, 2020. The entirety of each of the above-mentioned patent applications is hereby incorporated by reference herein and made a part of this specification.

BACKGROUND

Technical Field

The application relates to the field of biomedical technology, and in particular, to a method for the efficient expression, purification and application of a recombinant fusion protein of MANNase and homologues thereof and GLP-1.

Description of Related Art

Diabetes is one of the prevalent diseases that seriously threaten human life and health in modern society. Diabetes is an endocrine metabolic syndrome characterized by chronic hyperglycemia. According to the National Health and Family Planning Commission, 50.1% of adults are currently in the early stage of diabetes, and they may become new diabetic patients sooner or later. More data show that the prevalence of diabetes of China has grown rapidly in recent decades: from 0.67% in the 1980s to 11.6% in 2010, an increase of 17 times with the trend in a younger age.

In recent years, Glucagon-Like peptide-1 (GLP-1) not only have excellent hypoglycemic effects, but also have the characteristics of controlling weight, regulating blood lipids, and improving the function of islet β cells. At the same time, the incidence of adverse reactions of hypoglycemia is low. The excellent effects of GLP-1 and its analogs in treating type 2 diabetes and weight loss make it have gradually occupied an important position in the diabetic therapy market in recent years. The structure of the GLP-1 is usually modified to extend its half-life. There are two types of long-term GLP-1 analogs that have been listed on the market, both of which are combined with macromolecular proteins, namely Dulaglutide and Albiglutide. The former is a combination of G4 immune albumin, the latter is a combination of serum albumin, which extend the half-life of this peptide drug. Therefore, these drugs only need to be administrated once a week. However, Albiglutide and Dulaglutide still depend on injection once a week, which cannot achieve the limitations of oral administration. After injection, there will be adverse reactions of injecting site and nausea, vomiting and abdominal pain and other gastrointestinal adverse reactions.

Mannan exists in various plants in nature. β-MANNase is the most important enzyme in the process of degradation of mannan, which is widely used in the industry. It can hydrolyze the mannan into mannan oligosaccharides. Due to the lack of corresponding enzymes in animals, mannan oligosaccharides cannot be fully degraded, but they can be metabolized by probiotics in the digest tract, such as lactic acid bacteria and bifidobacteria. The products of metabolism include short-chain fatty acids (SCFA) such as acetic acid, propionic acid, and butyl. In turn, SCFA can have an important role in the body, such as inhibiting the growth of pathogenic bacteria, and supplying energy in muscles, kidneys, hearts, brains and other parts.

SUMMARY

In order to develop oral GLP-1 drug, this application proposes a method for the efficient expression and purification and application of a recombinant fusion protein of MANNase and homologues thereof and GLP-1 including their derivatives. The present application uses *Pichia pastoris* as an engineering strain, which can efficiently express mannanase (MANNase). By constitutes a fusion protein with MANNase and GLP-1, and then through high-density fermentation culture, the fusion protein can be efficiently expressed, which has both activities of MANNase and GLP-1. During the fermentation process, it induces expression through methanol. In the clearing solution, the target protein expression is high, and the purity is high. And the purification process is a filtering concentration, optimized to have high-efficiency with a low cost. More importantly, the fusion protein, either through injection or oral administration, exerts a similar hypoglycemic effect. The technical solution used by the present invention is as follows.

The technical solution used by the present invention is as follows.

A method for the efficient expression and purification of a recombinant fusion protein of MANNase and GLP-1 (including their derivatives), includes the following steps.

(1) ligating a gene sequence of the gene encoding GLP-1 and mannanase or homologues thereof to a *Pichia* expression plasmid (e.g. pPICZ-α), to obtain a recombinant expression vector;

(2) transforming the recombinant expression vector in step (1) into *Pichia pastoris* competent cells to construct recombinant engineering yeast;

(3) fermenting and culturing the reorganized engineering yeast (including fungi), to induce expression of the fusion protein;

(4) centrifuging the fermentation solution obtained from step (3), concentrating and dring the supernatant in turn to obtain the MANNase and homologues thereof and GLP-1 recombinant fusion protein.

In step (1), the plasmid is any one of pPICZαA, pPICZαB, and pPICZαC.

In step (3), the strain of *Pichia pastoris* is any one of X-33, GS115, KM71, SMD1168, SMD1168H.

In step (1), the sequences of the genes of encoding GLP-1 and mannanase are shown in SEQ ID NO. 1 and SEQ ID NO. 2, respectively.

In step (1), this was done as follows:

The target fragments encoding GLP-1 and mannanase or homologues thereof are cloned using primer pairs. After PCR amplification and double digestion, the obtained gene sequences encoding GLP-1 and mannanase or homologues thereof are ligated to the pPICZα plasmid, which completed the construction of the recombinant expression vector.

The primer pairs include a primer pair for amplifying the gene sequence encoding GLP-1 with mannanase. The sequences of the primer pair for amplifying the gene sequence encoding GLP-1 are shown in SEQ ID NO. 3 and shown in SEQ ID NO. 4. The sequences of the primer pair for amplifying the gene sequence encoding mannanase are shown in SEQ ID NO. 5 and SEQ ID NO. 6.

In step (3), the amino acid sequence of the fusion protein is shown in SEQ ID NO. 7.

In step (3), the specific steps for fermenting and culturing the recombinant engineering yeast and inducing the expression of the fusion protein MANNase-31P are as follow:

(S1) inoculating a single colony of the recombinant engineering yeast into a test tube of YPD liquid medium containing bleomycin, and incubating it with shaking at 30° C. and 200 rpm for 12 h; pouring the yeast solution into the YPD liquid medium and incubating it at 30° C. and 200 rpm for 12 h to obtain a primary seed solution.

(S2) Inoculating the primary seed solution in YPD medium at 10% inoculum and incubating for 22 h at 30° C. and 200 rpm to obtain a secondary seed solution; and (S3) adding the secondary seed solution into the fermentation culture medium at 10% inoculum for fermentation culture, and adding the induction agent when the $OD_{600}$ of the fermentation broth reaches above 60-120, and releasing the jar after induction and collecting the yeast by centrifugation.

In step (S3), the fermentation culture is a high density fermentation culture.

The inducer is methanol, and the volume percentage of the inducer added is 0.2%-3%.

In step (S4), the initial fermentation temperature is 30° C., the stirring speed is 300 rpm, the aeration rate is 4 L/min, and the pH is 5.5 when carrying out the fermentation culture.

In step (4), the specific steps for purifying, concentrating and drying the supernatant are as follows:

(SS1) taking the supernatant and filter it through a 0.8 um membrane, then a 0.2 um membrane, and collecting the filtrate;

(SS2) concentrating the filtrate first 10 times with an ultrafiltration membrane pack, and then 10 times with deionized water to obtain a concentrate; and (SS3) freeze-drying the concentrate to obtain the mannanase and homologues thereof and GLP-1 recombinant fusion protein.

Application of the mannanases and homologs thereof to GLP-1 recombinant fusion proteins in the preparation of drugs for the treatment of diabetes mellitus or high-fat, high-glucose diet-induced metabolic syndrome

*Pichia pastoris* is a methanolotrophic yeast that grows on a medium with methanol as the only carbon source. The alcohol oxidase gene AOX1 promoter on *Pichia pastoris* (*Saccharomyces cerevisiae*) is one of the most stringent promoters known. AOX1 plays an important role in methanol oxidation, and the alcohol oxidase protein which producing account for about 30% of the total soluble protein of the yeast when methanol is the only carbon source. Placing the exogenous gene under the control of the AOX1 promoter results in a high level of expression under methanol induction.

Mannanase is the most important enzyme in the process of mannan degradation and is widely used in industry to hydrolyze mannans into mannan oligosaccharides, which, as a prebiotic, can be absorbed and metabolized by probiotic microbes present in animals, such as lactic acid bacteria and bifidobacteria, and mannanase also has the property that it is not easily degraded by digestive enzymes. The inventors of this application have innovatively recombined the protein vector of mannanase and homologue thereof with GLP-1 to construct a recombinant protein. *Pichia pastoris* has a strict alcohol oxidase promoter regulatory mechanism that allows it to utilize methanol as the sole carbon source, with fast cell growth and easy high-density fermentation. Therefore, the inventors of this application use the recombinant protein high-secretion expression system of *Pichia pastoris* to efficiently express the recombinant protein MANNase-GLP-1 and homologues thereof. Through a series of isolation and purification methods, highly efficient, stable and low-cost oral hypoglycemic peptides is obtained, breaking through the common bottleneck that existing GLP analogue fusion proteins are not resistant to gastric acid and easily degraded by various GI proteases, and realizing the oral administration of hypoglycemia.

The beneficial effects of the present invention are as follow:

The efficient expression and purification of mannanase and homologues thereof with GLP-1 recombinant fusion protein is described in the present invention. First two target fragments are cloned from existing GLP-1 synthetic sequence and plasmid containing MANNase (mannanase) or its homologues respectively, then PCR amplification, followed by double digestion. The two fragments obtained are ligated to pPICZα plasmid and constructed to obtain a recombinant expression vector. The recombinant expression vector is transformed into the receptor cells of *Pichia pastoris* constructed to obtain recombinant engineering yeast. And the recombinant engineering yeast are fermentation induced to express the fusion protein. The invention uses *Pichia pastoris* as the engineering strain, which can express mannanase efficiently. And by forming a fusion protein of mannanase and homologues thereof with GLP-1 and high-density fermentation culture, the fusion protein can be secreted and expressed efficiently and has both mannanase and GLP-1 activity. The expression was induced by methanol during the fermentation of the present invention, and high expression of the target protein in the supernatant is obtained with high purity. The purification process of the present invention is only filtration concentration, which is a cost effective preparation method. The mannanase and homologues thereof and GLP-1 recombinant fusion protein described herein is suitable for both injectable and oral administration, which have good hypoglycemic and weight-reducing effects and are of good application in obese and pre-diabetic patients, while providing a basis for further studies on the mechanism of hypoglycemia and weight reduction of mannanase and homologues thereof and GLP-1 recombinant fusion protein.

BRIEF DESCRIPTION OF THE DRAWINGS

In order to more clearly illustrate the technical solutions in the embodiments or prior art of the invention, the following is a brief description of the accompanying drawings that need to be used in the description of the embodiments or prior art. Obviously, the accompanying drawings in the following description are only some embodiments of the present invention, and other drawings may be obtained from them without creative effort by a person of ordinary skill in the art.

DESCRIPTION OF THE EMBODIMENTS

In order to make the purpose, technical solutions and advantages of the present invention clearer, the technical solutions of the present invention are described in detail below. Obviously, the described embodiments are only a part of the embodiments of the invention, and not all of them. Based on the embodiments in the present invention, all other embodiments obtained by a person of ordinary skill in the art without making creative labor fall within the scope of protection of the present invention.

The YPD medium, fermentation medium and other reagents involved in the following examples are commercially available products known to those skilled in the art.

Embodiment 1

This embodiment provides a method for the efficient expression and purification of a recombinant fusion protein of mannanase and GLP-1 (MANNase-GLP-1), including the steps as follow.

(1) The target fragments encoding GLP-1 and mannanase were cloned using primer pairs, amplified by PCR and then double digested, after which the obtained gene sequences encoding GLP-1 and mannanase were ligated to the pPICZαA plasmid to construct a recombinant expression vector pPICZαA-MANNase-31P.

The sequences of the genes encoding GLP-1 and mannanase are shown in SEQ ID NO. 1 and SEQ ID NO. 2, respectively. The sequences of the primer pair for amplifying the gene sequence encoding GLP-1 are shown in SEQ ID NO. 3 and shown in SEQ ID NO. 4. The sequences of the primer pair for amplifying the gene sequence encoding mannanase are shown in SEQ ID NO. 5 and SEQ ID NO. 6. The amino acid sequence of said fusion protein MANNase-31P is shown in SEQ ID NO.7.

(2) the recombinant expression vector in step (1) was transformed into *Pichia pastoris* X-33 competent cells to construct recombinant engineering yeast MANNase-31P-X-33.

(3) The reorganized engineering yeast was fermented and cultured to induce expression of the fusion protein MANNase-31P. The specific steps were as follow.

Seed solution preparation: A single colony of the recombinant engineering yeast MANNase-31P-X-33 was inoculated into a test tube of 5 ml of YPD liquid medium containing bleomycin, incubating which with shaking at 30° C. and 200 rpm for 12 h. The yeast solution was poured into 50 ml of YPD liquid medium, incubating which at 30° C. and 200 rpm for 12 h to obtain a primary seed solution. The primary seed solution was inoculated in 500 ml of YPD medium at 10% inoculum, incubating which for 22 h at 30° C. and 200 rpm to obtain a secondary seed solution.

Figure 1:
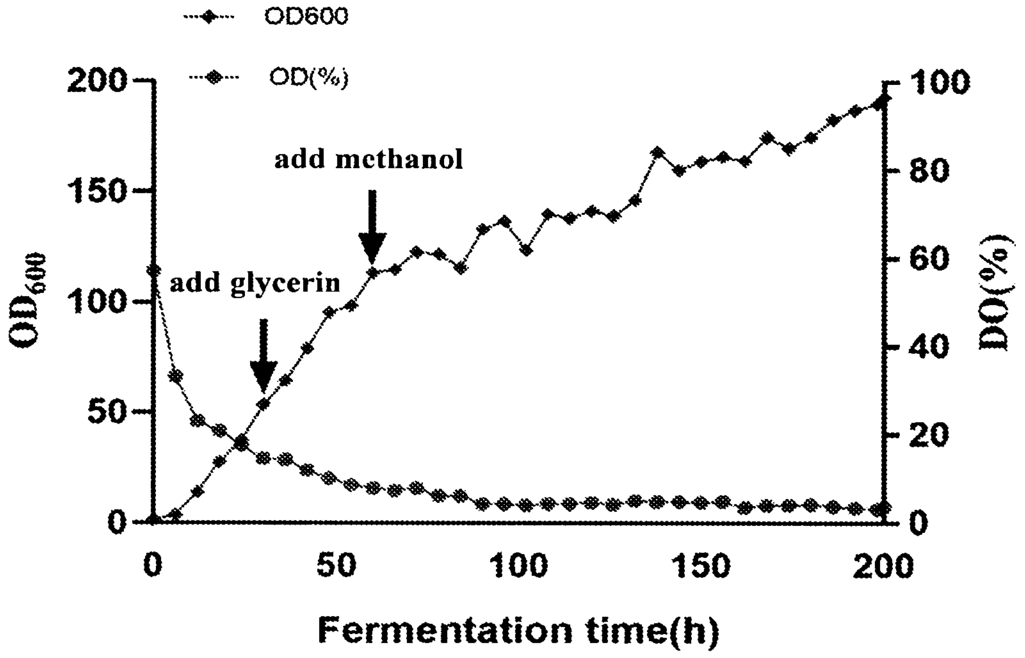
FIG. 1 is a fermentation curve diagram of the recombinant engineering yeast MANNase-31P-X-33 as described in Example 1 of the present invention.
Figure 2:
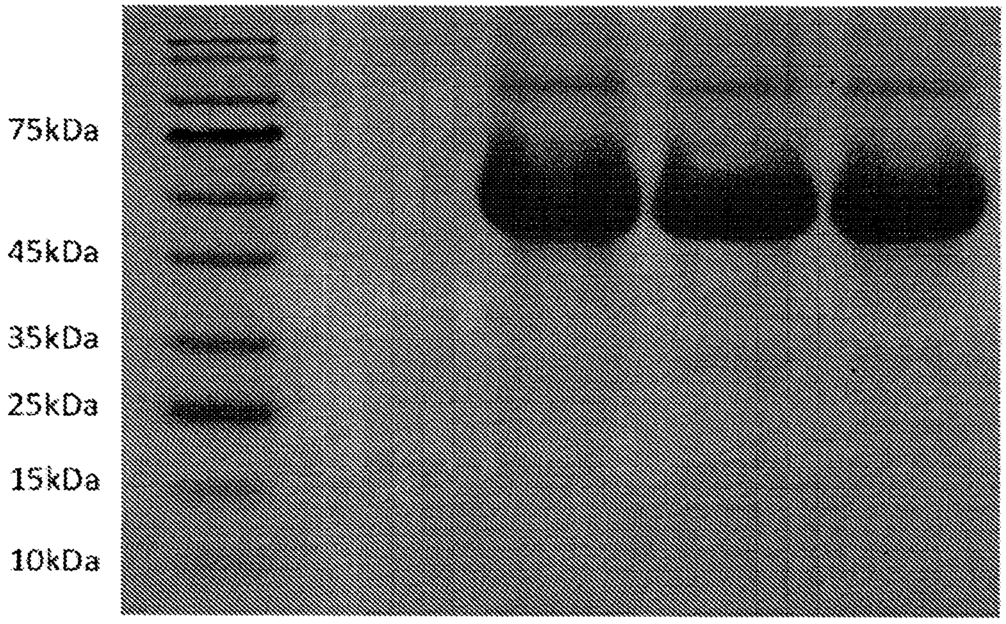
FIG. 2 is a schematic representation of the expression of the recombinant engineering yeast MANNase-31P-X-33 as described in Example 1 of the present invention.

Fermentation tank culture: The secondary seed solution was added to 4.5 L fermentation medium (7.5 L fermentation tank) at 10% inoculum for high density fermentation culture. The initial fermentation temperature is 30° C., the stirring speed is 300 rpm, the aeration rate is 4 L/min, and the pH is 5.5. The fermentation process includes four stages, the first stage was the growth stage with glycerol as the basic carbon source, mainly for the initial accumulation of cell biomass. With the gradual increase in the density of the yeast, the dissolved oxygen of the medium would rise rapidly, at this time to enter the glycerol replenishment stage, through the flow of glycerol to provide a carbon source, the yeast continued to grow, the dissolved oxygen was maintained at more than 20%. When the density of the yeast reaches 60 OD, after a 2 h starvation period, it entered the methanol induction phase. When the $OD_{600}$ of the fermentation broth reached above 60, the induction agent methanol was added and the percentage of methanol in the volume of the fermentation broth was 0.2%. During the period, the $OD_{600}$ value of the fermentation broth was measured by sampling every four hours, and the samples were kept for SDS-PAGE electrophoresis to detect the protein expression, as shown in FIG. 1 and FIG. 2 (indicated by arrows). As can be seen in the figures, the expression of the target protein was substantially increased. After 5 days of induction, the target protein was secreted into the extracellular, and the fermentation broth was collected from the tank after induction, and the supernatant was collected after centrifugation at 6000 rpm for 15 min. The content of the target protein in the supernatant was about 1-2 mg/ml.

(4) The supernatant obtained from step (3) was purified, concentrated, and dried in turn to obtain the recombinant MANNase-GLP-1.

The specific steps for purification, concentration and drying of the supernatant were as follows:

(SS1) taking the supernatant and filter it through a 0.8 um membrane, then a 0.2 um membrane, and collecting the filtrate;

(SS2) concentrating the filtrate (about 3 L) first 10 times with an 10 kd ultrafiltration membrane pack, and then 10 times with 3 L of deionized water to obtain a concentrate;

(SS3) freeze-drying the concentrate to obtain the recombinant MANNase-GLP-1.

Embodiment 2

This embodiment provides a method for the efficient expression and purification of a recombinant fusion protein of mannanase and GLP-1, including the steps as follow.

(1) The target fragments encoding GLP-1 and mannanase were cloned using primer pairs, amplified by PCR and then double digested, after which the obtained gene sequences encoding GLP-1 and mannanase were ligated to the pPICZαB plasmid to construct a recombinant expression vector pPICZαB-MANNase-31P.

The sequences of the genes encoding GLP-1 and mannanase are shown in SEQ ID NO. 1 and SEQ ID NO. 2, respectively. The sequences of the primer pair for amplifying the gene sequence encoding GLP-1 are shown in SEQ ID NO. 3 and shown in SEQ ID NO. 4. The sequences of the primer pair for amplifying the gene sequence encoding mannanase are shown in SEQ ID NO. 5 and SEQ ID NO. 6. The amino acid sequence of said fusion protein MANNase-31P is shown in SEQ ID NO.7.

(2) the recombinant expression vector in step (1) was transformed into *Pichia pastoris* GS115 competent cells to construct recombinant engineering yeast MANNase-31P-GS115.

(3) The recombinant engineering yeast was fermented and cultured to induce expression of the fusion protein MANNase-31P. The specific steps were as follow.

Seed solution preparation: A single colony of the recombinant engineering yeast MANNase-31P-GS115 was inoculated into a test tube of 5 ml of YPD liquid medium containing bleomycin, incubating which with shaking at 30° C. and 200 rpm for 12 h. The yeast solution was poured into 50 ml of YPD liquid medium, incubating which at 30° C. and 200 rpm for 12 h to obtain a primary seed solution. The primary seed solution was inoculated in 500 ml of YPD medium at 10% inoculum, incubating which for 22 h at 30° C. and 200 rpm to obtain a secondary seed solution.

Fermentation tank culture: The secondary seed solution was added to 4.5 L fermentation medium (7.5 L fermentation tank) at 10% inoculum for high density fermentation culture. The initial fermentation temperature is 30° C., the stirring speed is 300 rpm, the aeration rate is 4 L/min, and the pH is 5.5. The fermentation process includes four stages, the first stage was the growth stage with glycerol as the basic carbon source, mainly for the initial accumulation of cell biomass. With the gradual increase in the density of the yeast, the dissolved oxygen of the medium would rise rapidly, at this time to enter the glycerol replenishment stage, through the flow of glycerol to provide a carbon source, the yeast continued to grow, the dissolved oxygen was maintained at more than 20%. When the density of the yeast reaches 120 $OD_{600}$, after a 5 h starvation period, it entered the methanol induction phase. When the $OD_{600}$ of the fermentation broth reached above 120, the induction agent methanol was added and the percentage of methanol in the volume of the fermentation broth was 3%. During the period, the $OD_{600}$ value of the fermentation broth was measured by sampling every four hours, and the samples were kept for SDS-PAGE electrophoresis to detect the protein expression. After 5 days of induction, the target protein was secreted into the extracellular, and the fermentation broth was collected from the tank after induction, and the supernatant was collected after centrifugation at 6000 rpm for 15 min. The content of the target protein in the supernatant was about 1-2 mg/ml.

(4) The supernatant obtained from step (3) was purified, concentrated, and dried in turn to obtain the recombinant MANNase-GLP-1.

The specific steps for purification, concentration and drying of the supernatant were as follows:

(SS1) taking the supernatant and filter it through a 0.8 um membrane, then a 0.2 um membrane, and collecting the filtrate;

(SS2) concentrating the filtrate (about 3 L) first 10 times with an 10 kd ultrafiltration membrane pack, and then 10 times with 3 L of deionized water to obtain a concentrate;

(SS3) freeze-drying the concentrate to obtain the recombinant MANNase-GLP-1.

Embodiment 3

This embodiment provides a method for the efficient expression and purification of a recombinant fusion protein of mannanase and GLP-1, including the steps as follow.

(1) The target fragments encoding GLP-1 and mannanase were cloned using primer pairs, amplified by PCR and then double digested, after which the obtained gene sequences encoding GLP-1 and mannanase were ligated to the pPICZαC plasmid to construct a recombinant expression vector pPICZαC-MANNase-31P.

The sequences of the genes encoding GLP-1 and mannanase are shown in SEQ ID NO. 1 and SEQ ID NO. 2, respectively. The sequences of the primer pair for amplifying the gene sequence encoding GLP-1 are shown in SEQ ID NO. 3 and shown in SEQ ID NO. 4. The sequences of the primer pair for amplifying the gene sequence encoding mannanase are shown in SEQ ID NO. 5 and SEQ ID NO. 6. The amino acid sequence of said fusion protein MANNase-31P is shown in SEQ ID NO.7.

(2) the recombinant expression vector in step (1) was transformed into *Pichia pastoris* KM71 competent cells to construct recombinant engineering yeast MANNase-31P-KM71.

(3) The recombinant engineering yeast was fermented and cultured to induce expression of the fusion protein. The specific steps were as follow.

Seed solution preparation: A single colony of the recombinant engineering yeast MANNase-31P-KM71 was inoculated into a test tube of 5 ml of YPD liquid medium containing bleomycin, incubating which with shaking at 30° C. and 200 rpm for 12 h. The yeast solution was poured into 50 ml of YPD liquid medium, incubating which at 30° C. and 200 rpm for 12 h to obtain a primary seed solution. The primary seed solution was inoculated in 500 ml of YPD medium at 10% inoculum, incubating which for 22 h at 30° C. and 200 rpm to obtain a secondary seed solution.

Fermentation tank culture: The secondary seed solution was added to 4.5 L fermentation medium (7.5 L fermentation tank) at 10% inoculum for high density fermentation culture. The initial fermentation temperature is 30° C., the stirring speed is 300 rpm, the aeration rate is 4 L/min, and the pH is 5.5. The fermentation process includes four stages, the first stage was the growth stage with glycerol as the basic carbon source, mainly for the initial accumulation of cell biomass. With the gradual increase in the density of the yeast, the dissolved oxygen of the medium would rise rapidly, at this time to enter the glycerol replenishment stage, through the flow of glycerol to provide a carbon source, the yeast continued to grow, the dissolved oxygen was maintained at more than 20%. When the density of the yeast reaches 90 $OD_{600}$, after a 3.5 h starvation period, it entered the methanol induction phase. When the $OD_{600}$ of the fermentation broth reached above 90, the induction agent methanol was added and the percentage of methanol in the volume of the fermentation broth was 1.6%. During the period, the $OD_{600}$ value of the fermentation broth was measured by sampling every four hours, and the samples were kept for SDS-PAGE electrophoresis to detect the protein expression, as shown in FIG. 1 and FIG. 2 (indicated by arrows). As can be seen in the figures, the expression of the target protein was substantially increased. After 5 days of induction, the target protein was secreted into the extracellular, and the fermentation broth was collected from the tank after induction, and the supernatant was collected after centrifugation at 6000 rpm for 15 min. The content of the target protein in the supernatant was about 1-2 mg/ml.

(4) The supernatant obtained from step (3) was purified, concentrated, and dried in turn to obtain the recombinant MANNase-GLP-1.

The specific steps for purification, concentration and drying of the supernatant were as follows:

(SS1) taking the supernatant and filter it through a 0.8 um membrane, then a 0.2 um membrane, and collecting the filtrate;

(SS2) concentrating the filtrate (about 3 L) first 10 times with an 10 kd ultrafiltration membrane pack, and then 10 times with 3 L of deionized water to obtain a concentrate;

(SS3) freeze-drying the concentrate to obtain the recombinant MANNase-GLP-1.

Embodiment 4

The only difference between Embodiment 4 and Embodiment 1 is that in step (3), the strain of *Pichia pastoris* is SMD1168, but the rest is the same as in Embodiment 1.

Embodiment 5

The only difference between Embodiment 5 and Embodiment 1 is that in step (3), the strain of *Pichia pastoris* is SMD1168H, but the rest is the same as in Embodiment 1.

Embodiment 6

The only difference between Embodiment 6 and Embodiment 1 is that in step (3), the steps of fermentation and culture and induction of expression of the recombinant engineering yeast are different. The specific steps for fermentation and culture of recombinant engineering yeast and induction of expression of the fusion protein MANNase-31P in this embodiment were as follow.

Figure 10:
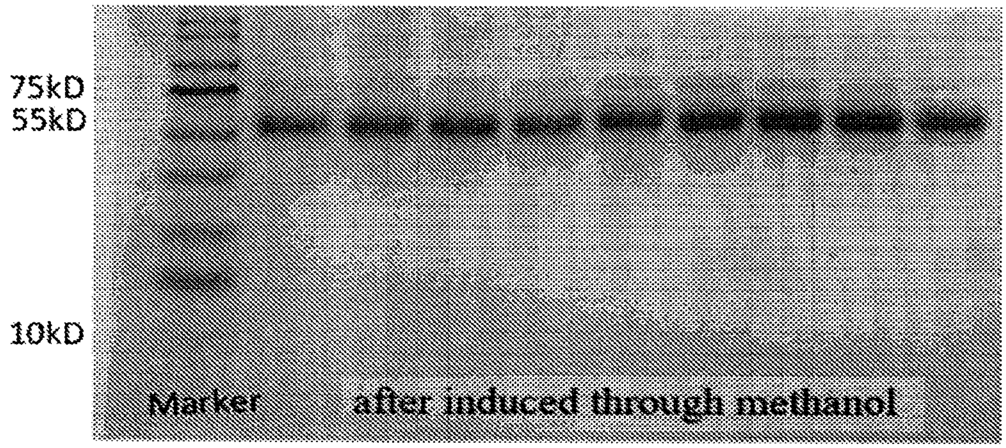
FIG. 10 is a schematic representation of the expression of the recombinant yeast MANNase-31P-X-33 as described in Example 3 of the present invention.

A single colony of the successfully constructed engineering yeast for expression of *Pichia pastoris* MANNase-31P-X-33 were picked and inoculated into 5 ml of YPD liquid medium and incubated overnight at 30° C. and 250 rpm in a shaker. The cultured strain was inoculated into BMGY medium at 1% and continued to shake for 24 h, after which the yeast was transferred into BMMY medium and the $OD_{600}$ was adjusted to about 1.0, and the culture was continued to be induced in a shaker at 30° C. and 200 rpm, with methanol added at 0.5% by volume every 24 h for 4 days. The amount of target protein in the supernatant was about 0.2 mg/ml. The protein expression by SDS-PAGE electrophoresis is shown in FIG. 10.

Experimental Example

1. Application of Recombinant MANNase-GLP-1 Obtained in Embodiment 1 in High-Fat and High-Sugar Diet-Induced Metabolic Syndrome 1-1) Construction of a Mouse Model of Metabolic Syndrome Induced by High-Fat and High-Sugar Diet One hundred 6-week-old (18-20 g) C57-6J mice (4-6 weeks old, male) were housed in separate cages with controlled animal room temperature of 25±2° C., humidity of 50±10%, and a 12-h light and 12-h dark cycle to acclimatize to the environment for one week. The mice were randomly divided into cages of 5-6 mice/group. Body weight and fasting blood-glucose (FBG) were measured after 12 h of fasting. The control group was fed with standard chow, and the model group was fed with high-fat, high-sugar (HFSD) chow for 24 weeks. After finishing, the body weight and FBG of each group of mice were measured.

Figure 3:
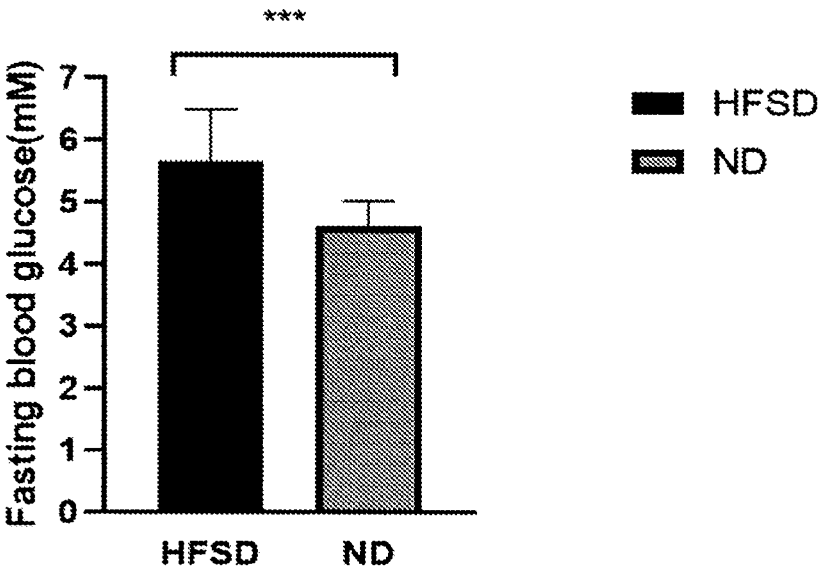
FIG. 3 is a schematic representation of the comparative statistical analysis of the blood glucose levels in the control and model mice.
Figure 4:
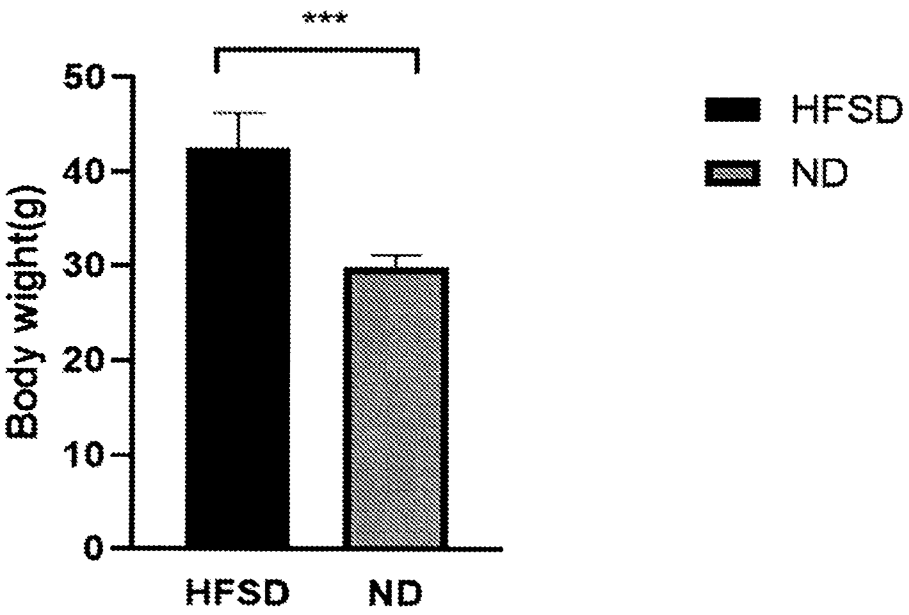
FIG. 4 is a schematic representation of the comparative statistical analysis of the body weight levels in the control and model mice.

The body weight of mice on high-fat and high-sugar diet was about 42.5 g and that of mice on normal diet was about 30 g. The fasting blood glucose of mice on high-fat and high-sugar diet was about 5.67 and that of mice on normal diet was 4.62, with statistical differences (*P<0.05, P<0.01, *P<0.001). As shown in FIGS. 3 and 4 below, it can be seen that: After C57-6J mice induced by high-fat and high-sugar diet for 24 weeks, their body weight exceeded normal diet by 41.67%, meeting the criteria of obesity model (20%). C57-6J mice induced by high-fat and high-sugar diet had significantly higher fasting blood glucose than normal diet by 22.73%.

Figure 5:
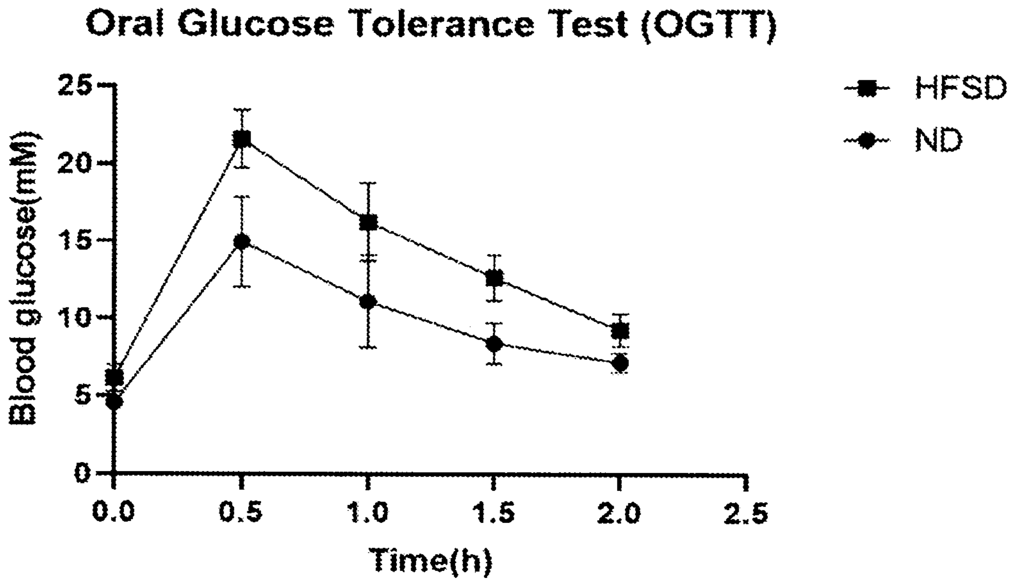
FIG. 5 is a schematic representation of the comparison of glucose tolerance curves between control and model mice.

The oral glucose tolerance (OGTT) curves were obtained from regular diet mice and high-fat and high-sugar mice after overnight fasting for 12 h and gavage of D-glucose at 2 g/kg (body weight) at 0, 0.5, 1.0, 1.5, 2.0, and 2.5 h, respectively, as shown in FIG. 5. It can be seen that the glucose tolerance was significantly impaired after 24 weeks of high-fat and high-sugar diet induction. The oral glucose tolerance test is a glucose stress test. Impaired glucose tolerance indicates a decrease in pancreatic islet beta cell function and the body's ability to regulate blood glucose, and is used to diagnose mild hyperglycemia in prediabetes.

Figure 6:
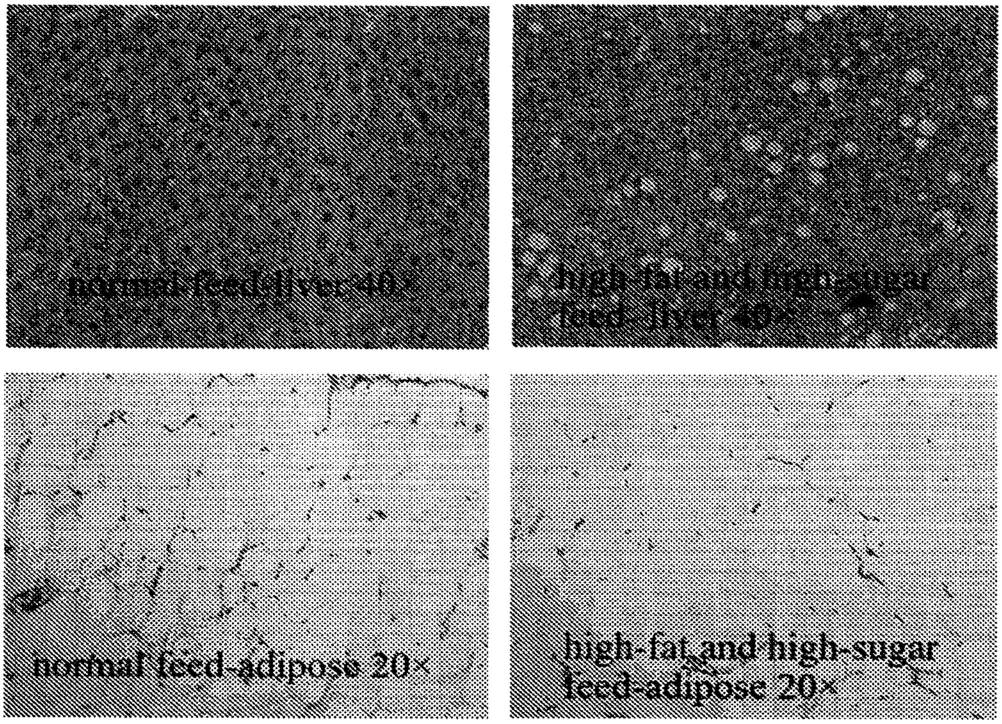
FIG. 6 is a schematic representation of the HE stained sections of liver and adipose tissue of control and model mice.

HE-stained sections of liver and adipose tissue from mice on a high-fat, high-sugar diet and mice on a normal diet were analyzed. As shown in FIG. 6, it can be seen from the figure: mice on high-fat and high-sugar diets had significant fatty liver and there was also a significant difference in the size of adipocytes between the two groups.

After successful modeling, 11 animals/group were randomly grouped, plus the normal feed group, for subsequent gavage experiments.

Figure 7:
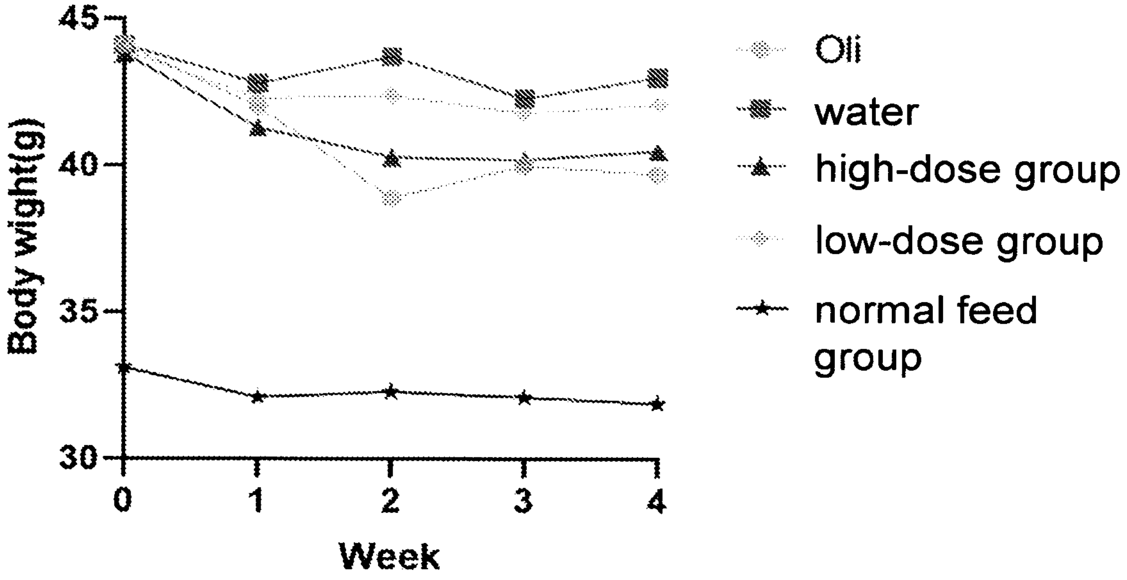
FIG. 7 is a schematic representation of the changes in body weight levels of mice tested at different times.
Figure 8:
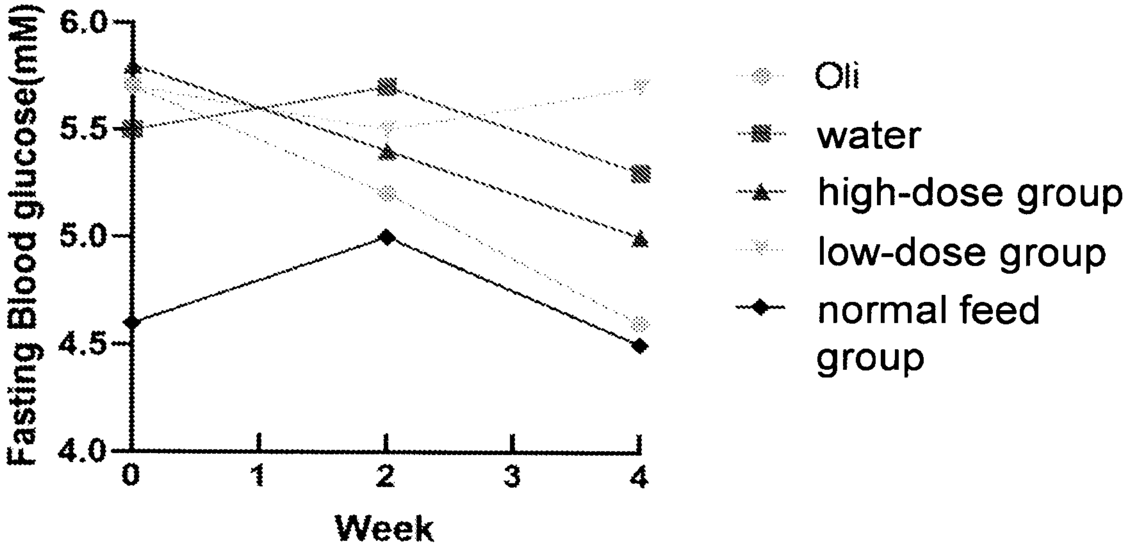
FIG. 8 is a schematic representation of the changes in blood glucose levels of mice tested at different times.

1-2) Effect of Oral Administration of MANNase-GLP-1 on High-Fat and High-Sugar Diet-Induced Metabolic Syndrome Mice were randomly divided into five groups, wherein fusion protein high-dose group (0.7 mg/kg-d), fusion protein-affected low-dose group (0.14 mg/kg-d), and 30 mg/kg orlistat were as positive control groups, and the normal feed control group and the high-fat, high-sugar feed as a negative control group were given the same volume of water. All mice were gavaged separately without any change in diet. Weekly weight changes were measured, and changes in fasting blood glucose were measured every two weeks. The results are shown in FIG. 7 and FIG. 8. It can be concluded that the MANNase-GLP-1 fusion protein described in Example 1 of the present invention has a significant weight reduction and hypoglycemic effect.

2. Effect of the Recombinant MANNase-GLP-1 Injection Administration on Type II Diabetes Mellitus Obtained in Embodiment 1

2-1) Construction of a Mouse Model of Type II Diabetes Mellitus.

Fifty 6-week-old (18-20 g) BALB/C mice (males) were randomly divided into cages in groups of 8 mice each. Body weight and fasting blood-glucose (FBG) were measured after 12 h of fasting. The control group was fed with standard chow for 4 weeks and the modeling group was fed with high-fat chow for 4 weeks, and then the body weight and FBG of each group were measured. After 12 h of fasting, STZ was injected intraperitoneally at a dose of 60 mg/kg-Bw for 3 days.

The body weight and FBG of the modeled mice were measured on the 3rd, 7th, 10th and 14th days after modeling, and mice with FBG≥11.1 mmol/L and stable for one week were selected as type II diabetic model mice, and 8 mice/group were randomly divided into cages for hypoglycemia experiments.

Figure 9:
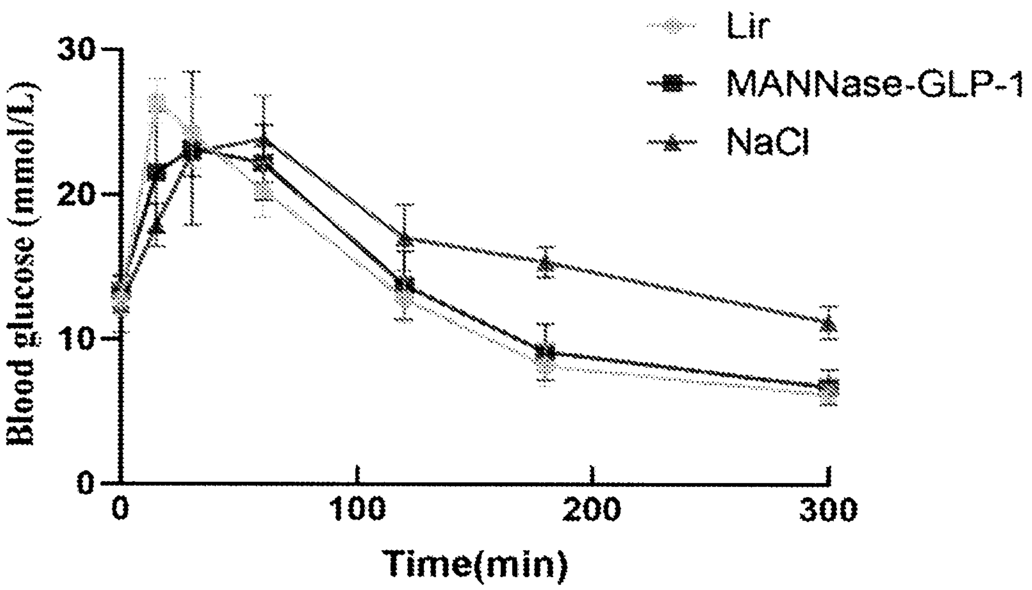
FIG. 9 is a schematic representation of the comparison of the effects of injectable administration on blood glucose levels in mice.

Mice were randomly divided into three groups: diabetic negative control group (saline), diabetic positive control group (Lir), and diabetic treatment group (MANNase-GLP-1), with 8 mice in each group. All mice were gavaged with D-glucose at 1.5 g/kg (body weight) after overnight fasting for 12 h, and then subcutaneously injected with (s.c.) MANNase-GLP-1 (250 ug/50 g), and blood was collected from the tail after 0, 15, 30, 60, 120, 180 min and 300 min after injection, and the blood glucose level was measured by Roche blood glucose test paper. The results are shown in FIG. 9.

The purpose of the present invention is to provide a method for the preparation of mannanase and homologues thereof and GLP-1 recombinant fusion protein capable of improving body weight and blood glucose in patients with high-fat and high-glucose diet-induced metabolic syndrome. Through genetic recombination technology, soluble proteins are obtained by using high density fermentation of *Pichia pastoris* to induce secretory expression, followed by isolation and purification by filtration and concentration to obtain high yield of target proteins. The high fermentation expression and simple isolation steps solve the limitations of the current GLP-1 analogs such as low drug yield, high cost and the need for frequent injections. More importantly, the fusion protein has hypoglycemic effect not only by injection, but also by oral administration for hypoglycemia and weight reduction, which has good application value in obese and pre-diabetic patients. It also provides a basis for further research on the mechanism of hypoglycemia and weight loss of mannanase and homologues thereof with GLP-1 recombinant fusion protein.

The above described is only a specific implementation of the present invention, but the scope of protection of the present invention is not limited to it, and any changes or substitutions that can be readily thought of by any person skilled in the art within the technical scope disclosed by the present invention shall be covered by the scope of protection of the present invention. Therefore, the scope of protection of the present invention shall be subject to the scope of protection of the said claims.

INDUSTRIAL PRACTICALITY

This application proposes an efficient expression and purification method and application of MANNase and homologues thereof and GLP-1 recombinant fusion protein. Through genetic recombination technology, soluble proteins are obtained by using high density fermentation of *Pichia pastoris* to induce secretory expression, followed by isolation and purification by filtration and concentration to obtain high yield of target proteins. The high fermentation expression and simple isolation steps solve the limitations of the current GLP-1 analogs such as low drug yield, high cost and the need for frequent injections. More importantly, the fusion protein has hypoglycemic effect not only by injection, but also by oral administration for hypoglycemia and weight reduction, which has good application value in obese and pre-diabetic patients. It also provides a basis for further research on the mechanism of hypoglycemia and weight loss of mannanase and its homologues with GLP-1 recombinant fusion protein.

What is claimed is:

1. A method for the efficient expression and purification of a recombinant fusion protein of mannanase (MANNase) and Glucagon-Like peptide-1 (GLP-1), comprising the following steps:

(1) ligating gene sequences of the genes encoding GLP-1 and mannanase to a pPICZ-α plasmid, to obtain a recombinant expression vector;

(2) transforming the recombinant expression vector in step (1) into *Pichia pastoris* competent cells to construct a recombinant engineered yeast;

(3) fermenting and culturing the recombinant engineered yeast, to induce expression of the recombinant MANNase-GLP-1 fusion protein;

(4) centrifuging a fermentation broth obtained from step (3) to obtain a supernatant, and purifying, concentrating, and drying the supernatant in turn to obtain the recombinant MANNase-GLP-1 fusion protein, wherein the recombinant MANNase-GLP-1 fusion protein comprises the amino acid sequence of SEQ ID NO. 7.

2. The method according to claim 1, wherein in step (1), the genes encoding GLP-1 and mannanase comprise the nucleic acid sequence of SEQ ID NO. 1 and SEQ ID NO. 2, respectively.

3. The method according to claim 1, wherein step (1) further comprises:

cloning target fragments encoding GLP-1 and mannanase using primer pairs by PCR amplification and double digestion to obtain the gene sequences encoding GLP-1 and mannanase that are ligated to the pPICZα plasmid.

4. The method according to claim 3, wherein the primer pairs comprise a primer pair for amplifying the gene sequence encoding GLP-1 and a primer pair for amplifying the gene sequence encoding mannanase, wherein the primer pair for amplifying the gene sequence encoding GLP-1 comprise the nucleic acid sequence of SEQ ID NO. 3 and SEQ ID NO. 4, and the primer pair for amplifying the gene sequence encoding mannanase comprise the nucleic acid sequence of SEQ ID NO. 5 and SEQ ID NO. 6.

5. The method according to claim 1, wherein in step (3), the steps for fermenting and culturing the recombinant engineered yeast and inducing expression of the recombinant MANNase-GLP-1 fusion protein are as follows:

(S1) inoculating a single colony of the recombinant engineered yeast into a test tube of Yeast Extract Peptone Dextrose (YPD) liquid medium containing bleomycin, and incubating it with shaking at 30° C. and 200 rpm for 12 h to obtain a recombinant engineered yeast solution; pouring the recombinant engineered yeast solution into YPD liquid medium and incubating it at 30° C. and 200 rpm for 12 h to obtain a primary seed solution;

(S2) inoculating the primary seed solution in YPD medium at 10% inoculum and incubating for 22 h at 30° C. and 200 rpm to obtain a secondary seed solution; and (S3) adding the secondary seed solution into a fermentation culture medium at 10% inoculum for fermentation culture, and adding an induction agent when the fermentation broth reaches an OD600 above 60-120, and collecting the recombinant engineered yeast by centrifugation.

6. The method according to claim 5, wherein in step (S3), the fermentation culture is a high density fermentation culture; and the induction agent is methanol, and a volume percentage of the induction agent added is 0.2%-3%.

7. The method according to claim 5, wherein in step (S3), an initial fermentation temperature is 30° C., a stirring speed is 300 rpm, an aeration rate is 4 L/min, and a pH is 5.5 when carrying out the fermentation culture.

8. The method according to claim 1, wherein in step (4), the steps for purifying, concentrating and drying the supernatant are as follows:

(SS1) filtering the supernatant through a 0.8 μm membrane and a 0.2 μm membrane, and collecting a filtrate;

(SS2) concentrating the filtrate 10 times with an ultrafiltration membrane pack, and then 10 times with deionized water to obtain a concentrate; and (SS3) freeze-drying the concentrate to obtain the recombinant MANNase-GLP-1 fusion protein.

9. A method for treating diabetes or high-fat, high-glucose diet-induced metabolic syndrome, comprising:

orally administering to a subject in need thereof a drug preparation comprising a recombinant MANNase-GLP-1 fusion protein comprising the amino acid sequence of SEQ ID NO. 7.

* * * * *

SEQUENCE LISTING

```
<160> NUMBER OF SEQ ID NOS: 7

<210> SEQ ID NO 1
<211> LENGTH: 93
<212> TYPE: DNA
<213> ORGANISM: Artificial Sequence
<220> FEATURE:
<223> OTHER INFORMATION: gene sequence of encoding GLP-1

<400> SEQUENCE: 1

cacgctgaag gtaccttcac ctctgacgtt tcttcttacc tggaaggtca ggctgctaaa      60

gaattcatcg cttggctggt tcgtggtcgt ggt                                   93


<210> SEQ ID NO 2
<211> LENGTH: 1089
<212> TYPE: DNA
<213> ORGANISM: Artificial Sequence
<220> FEATURE:
<223> OTHER INFORMATION: gene sequence of encoding mannanase

<400> SEQUENCE: 2

ttgccaaagg cttctccagc tccatctact tcttcttctt ctgcttctac ttcttttgct      60

tctacttctg gtttgcaatt tactattgat ggtgaaactg gttactttgc tggtactaac     120

tcttactgga ttggtttttt gactgatgat tctgatgttg atttggttat gtctcatttg     180

aagtcttctg gtttgaagat tttgagagtt tggggtttta acgatgttac tactcaacca     240

tcttctggta ctgtttggta ccaattgcat caagatggta agtctactat taacactggt     300

gctgatggtt tgcaaagatt ggattacgtt gtttcttctg ctgaacaaca tggtattaag     360

ttgattatta actttgttaa ctactggact gattacggtg gtatgtctgc ttacgtttct     420
```

```
gcttacggtg gttctgatga aactgatttt tacacttctg atactatgca atctgcttac    480

caaacttaca ttaagactgt tgttgaaaga tactctaact cttctgctgt tttgcttgg    540

gaattggcta acgaaccaag atgtccatct tgtgatacta ctgttttgta cgattggatt    600

gaaaagactt ctaagtttat taagggtttg gatgctgatc atatggtttg tattggtgat    660

gaaggttttg gtttgaacac tgattctgat ggttcttacc cataccaatt tgctgaaggt    720

ttgaacttta ctatgaactt gggtattgat actattgatt ttgctacttt gcatttgtac    780

ccagattctt ggggtacttc tgatgattgg ggtaacggtt ggatttctgc tcatggtgct    840

gcttgtaagg ctgctggtaa gccatgtttg ttggaagaat acggtgttac ttctaaccat    900

tgttctgttg aatctccatg gcaacaaact gctttgaaca ctactggtgt ttctgctgat    960

ttgttttggc aatacggtga tgatttgtct actggtgaat ctccagatga tggtaacact   1020

atttactacg gtacttctga ttacgaatgt ttggttactg atcatgttgc tgctattgat   1080

tctgcttaa                                                            1089


<210> SEQ ID NO 3
<211> LENGTH: 29
<212> TYPE: DNA
<213> ORGANISM: Artificial Sequence
<220> FEATURE:
<223> OTHER INFORMATION: primer for amplifying gene sequence of encoding
      GLP-1

<400> SEQUENCE: 3

cgggatccga ctacaaggac gacgacgac                                        29


<210> SEQ ID NO 4
<211> LENGTH: 28
<212> TYPE: DNA
<213> ORGANISM: Artificial Sequence
<220> FEATURE:
<223> OTHER INFORMATION: primer for amplifying gene sequence of encoding
      GLP-1

<400> SEQUENCE: 4

gctctagatt aacctctacc tctaacca                                         28


<210> SEQ ID NO 5
<211> LENGTH: 28
<212> TYPE: DNA
<213> ORGANISM: Artificial Sequence
<220> FEATURE:
<223> OTHER INFORMATION: primer for amplifying gene sequence of encoding
      mannanase

<400> SEQUENCE: 5

cggaattctt gccaaaggct tctccagc                                         28


<210> SEQ ID NO 6
<211> LENGTH: 28
<212> TYPE: DNA
<213> ORGANISM: Artificial Sequence
<220> FEATURE:
<223> OTHER INFORMATION: primer for amplifying gene sequence of encoding
      mannanase

<400> SEQUENCE: 6

cgggatccag cagaatcaat agcagcaa                                         28


<210> SEQ ID NO 7
<211> LENGTH: 401
```

-continued

<212> TYPE: PRT
<213> ORGANISM: Artificial Sequence
<220> FEATURE:
<223> OTHER INFORMATION: recombinant fusion protein of MANNase and homologues thereof and GLP-1

<400> SEQUENCE: 7

```
Leu Pro Lys Ala Ser Pro Ala Pro Ser Thr Ser Ser Ser Ser Ala Ser
1               5                   10                  15

Thr Ser Phe Ala Ser Thr Ser Gly Leu Gln Phe Thr Ile Asp Gly Glu
            20                  25                  30

Thr Gly Tyr Phe Ala Gly Thr Asn Ser Tyr Trp Ile Gly Phe Leu Thr
        35                  40                  45

Asp Asp Ser Asp Val Asp Leu Val Met Ser His Leu Lys Ser Ser Gly
    50                  55                  60

Leu Lys Ile Leu Arg Val Trp Gly Phe Asn Asp Val Thr Thr Gln Pro
65                  70                  75                  80

Ser Ser Gly Thr Val Trp Tyr Gln Leu His Gln Asp Gly Lys Ser Thr
                85                  90                  95

Ile Asn Thr Gly Ala Asp Gly Leu Gln Arg Leu Asp Tyr Val Val Ser
            100                 105                 110

Ser Ala Glu Gln His Gly Ile Lys Leu Ile Ile Asn Phe Val Asn Tyr
        115                 120                 125

Trp Thr Asp Tyr Gly Gly Met Ser Ala Tyr Val Ser Ala Tyr Gly Gly
    130                 135                 140

Ser Asp Glu Thr Asp Phe Tyr Thr Ser Asp Thr Met Gln Ser Ala Tyr
145                 150                 155                 160

Gln Thr Tyr Ile Lys Thr Val Val Glu Arg Tyr Ser Asn Ser Ser Ala
                165                 170                 175

Val Phe Ala Trp Glu Leu Ala Asn Glu Pro Arg Cys Pro Ser Cys Asp
            180                 185                 190

Thr Thr Val Leu Tyr Asp Trp Ile Glu Lys Thr Ser Lys Phe Ile Lys
        195                 200                 205

Gly Leu Asp Ala Asp His Met Val Cys Ile Gly Asp Glu Gly Phe Gly
    210                 215                 220

Leu Asn Thr Asp Ser Asp Gly Ser Tyr Pro Tyr Gln Phe Ala Glu Gly
225                 230                 235                 240

Leu Asn Phe Thr Met Asn Leu Gly Ile Asp Thr Ile Asp Phe Ala Thr
                245                 250                 255

Leu His Leu Tyr Pro Asp Ser Trp Gly Thr Ser Asp Asp Trp Gly Asn
            260                 265                 270

Gly Trp Ile Ser Ala His Gly Ala Ala Cys Lys Ala Ala Gly Lys Pro
        275                 280                 285

Cys Leu Leu Glu Glu Tyr Gly Val Thr Ser Asn His Cys Ser Val Glu
    290                 295                 300

Ser Pro Trp Gln Gln Thr Ala Leu Asn Thr Thr Gly Val Ser Ala Asp
305                 310                 315                 320

Leu Phe Trp Gln Tyr Gly Asp Asp Leu Ser Thr Gly Glu Ser Pro Asp
                325                 330                 335

Asp Gly Asn Thr Ile Tyr Tyr Gly Thr Ser Asp Tyr Glu Cys Leu Val
            340                 345                 350

Thr Asp His Val Ala Ala Ile Asp Ser Ala Asp Tyr Lys Asp Asp Asp
        355                 360                 365

Asp Lys His Ala Glu Gly Thr Phe Thr Ser Asp Val Ser Ser Tyr Leu
    370                 375                 380
```

-continued

```
Glu Gly Gln Ala Ala Lys Glu Phe Ile Ala Trp Leu Val Arg Gly Arg
385                 390                 395                 400

Gly
```